(12) United States Patent
Blank et al.

(10) Patent No.: US 10,028,751 B2
(45) Date of Patent: Jul. 24, 2018

(54) POSITIONING AND TEMPLATE SYSTEM FOR PREPARING A FEMUR FOR KNEE REPLACEMENT

(71) Applicant: Medevice Solutions, LLC, Springboro, OH (US)

(72) Inventors: Thomas W. Blank, Springboro, OH (US); Casel G. Burnett, Walton, KY (US); Daniel J. Dunaway, Dayton, OH (US); Lewis T. Ross, Franklin, OH (US)

(73) Assignee: MEDEVICE SOLUTIONS, LLC, Springboro, OH (US)

( * ) Notice: Subject to any disclaimer, the term of this patent is extended or adjusted under 35 U.S.C. 154(b) by 337 days.

(21) Appl. No.: 14/829,181

(22) Filed: Aug. 18, 2015

(65) Prior Publication Data

US 2016/0045204 A1 Feb. 18, 2016

Related U.S. Application Data

(60) Provisional application No. 62/038,588, filed on Aug. 18, 2014.

(51) Int. Cl.
*A61B 17/58* (2006.01)
*A61B 17/60* (2006.01)
*A61F 2/00* (2006.01)
*A61B 17/15* (2006.01)
*A61B 17/17* (2006.01)

(52) U.S. Cl.
CPC ........ *A61B 17/155* (2013.01); *A61B 17/1764* (2013.01)

(58) Field of Classification Search
None
See application file for complete search history.

(56) References Cited

U.S. PATENT DOCUMENTS

| | | | |
|---|---|---|---|
| 7,993,341 B2 | 8/2011 | Grimm et al. | |
| 8,323,288 B2 | 12/2012 | Zajac | |
| 2005/0203528 A1* | 9/2005 | Couture | A61B 17/154 606/86 R |
| 2008/0275451 A1* | 11/2008 | McAllister | A61B 17/155 606/87 |
| 2009/0099567 A1 | 4/2009 | Zajac | |

OTHER PUBLICATIONS

Zimmer, Inc., iAssist Knee Surgical Technique, Sep. 10, 2013, Rev. 5, 97-9001-101-00.
Zimmer, Inc., Nextgen Complete Knee Solution Surgical Technique for Cruciate Retaining Knees, 1995, Rev. 97-5970-102.

* cited by examiner

*Primary Examiner* — Sameh Boles
(74) *Attorney, Agent, or Firm* — Dinsmore & Shohl LLP

(57) ABSTRACT

A positioning and template system for preparing a femur for knee replacement. The system includes a datum block, a datum block placement assembly, and a cutting template assembly. The datum block placement assembly is reversibly attachable to the datum block. Further, the datum block placement assembly positions the datum block on the femur in a measured position relative to the transepicondylar axis of the femur when the datum block placement assembly is attached to the datum. Finally, the cutting template assembly is reversibly attachable to the datum block in place of the datum block placement assembly to correctly position the cutting template assembly for guiding femoral cuts in a knee replacement surgery.

19 Claims, 4 Drawing Sheets

POSITIONING AND TEMPLATE SYSTEM FOR PREPARING A FEMUR FOR KNEE REPLACEMENT

CROSS-REFERENCE TO RELATED APPLICATION

This invention claims the benefit of U.S. Provisional Application 62/038,588 filed Aug. 18, 2014, which is incorporated by reference herein in its entirety.

TECHNICAL FIELD

Embodiments of the present disclosure are generally related to devices and methods for artificial knee implant preparation, and are specifically related to instrumentation for locating and guiding femoral cuts in an artificial knee implant insertion surgical procedure.

BACKGROUND

Artificial knee implants fitted upon the patient's femur require precise cuts of the femur bone in order to insure a proper fit and alignment of the implant. The cuts to the femur must be accurate, precise and require a skilled surgeon's expertise to properly fit a replacement knee onto the patient's femur. Current procedures rely upon multiple cutting blocks and templates for cuts to be made to the femur. These cutting blocks are pinned to the face of the femur where the cuts are to be made, and a saw is used to cut on the template for the appropriate angles and lengths. This routinely requires the surgeon to move the pins throughout the process to allow the surgeon to make all the required cuts without interference from the pins. Generally, at a minimum a surgeon will need to pin and unpin the cutting templates seven times for a single procedure. Some cutting techniques require more movement of the pins for the cuts and consequently require more pinning and unpinning of the cutting templates. This requires additional time to perform the cutting procedure while in surgery, and consequently increases time in the operating room. Other methods of producing the appropriate femoral cuts include forming a cutting jig that is custom fabricated for an individual patient's anatomy. This method requires CT or MRI imagery scans and a 3-D jig or jigs to be custom fabricated for an individual patient based upon the images. The jig is then placed around the femur to guide the surgeon in making the required femoral cuts. However, formation of a custom jig using CT or MRI data is time consuming and costly and the custom jig is not adjustable or adaptable in the operating suite based on the patient's specific needs and anatomy at the time of surgery.

Accordingly, ongoing need exists for improved techniques and tools for cutting the femur in preparation for a full or partial knee implant. Of particular need is a system that will allow the surgeon to make all of the required femoral cuts without the shuffling of cutting block pins and multiple cutting templates.

SUMMARY

Embodiments of the present disclosure contemplate a positioning and template system for cutting the femur in preparation for the installation of a replacement knee implant. Utilization of embodiments of the positioning and template system as described and shown herein eliminates the repositioning of surgical pins during the process of cutting a femur in a knee replacement surgery. As previously stated, current technology generally requires no fewer than seven surgical pins to be inserted and removed throughout the surgical process of positioning as many as three sequential cutting jigs. This disclosure contemplates a device that utilizes a datum block in combination with a single cutting template for alignment and cutting of all femoral cuts. The single cutting template attached to the datum block removes the need for pin repositioning during the femoral cuts which saves time in the operating suite as well as improves accuracy and adjustability of implant positioning in the total knee replacement.

According to at least one embodiment, a positioning and template system for preparing a femur for knee replacement is provided. The system includes a datum block, a datum block placement assembly, and a cutting template assembly. The datum block placement assembly is reversibly attachable to the datum block. Further, while the datum block placement assembly is attached to the datum the datum block placement assembly, the datum block placement assembly positions the datum block on the femur in a measured position relative to the transepicondylar axis of the femur. Finally, the cutting template assembly is reversibly attachable to the datum block in place of the datum block placement assembly.

According to other embodiments, a method of preparing a femur for knee replacement is provided. The method includes positioning a datum block on the femur in a measured position relative to the transepicondylar axis of the femur with a datum block placement assembly. Additionally, the method includes securing the datum block to the femur. Further, the method includes removing the datum block placement assembly from the secured datum block and attaching a cutting template assembly comprising a cutting template to the secured datum block. Subsequently, the method includes cutting a distal femur cut, an anterior femur cut, a posterior femur cut, an anterior chamfer cut, and a posterior chamfer cut on the femur using a plurality of cutting template guide slots provided on the cutting template to define the position and angle of the distal femur cut, the anterior femur cut, the posterior femur cut, the anterior chamfer cut, and the posterior chamfer cut. Additionally, the plurality of cutting template guide slots are positioned such that repositioning of the cutting template between cuts is not required.

Figure 1A:
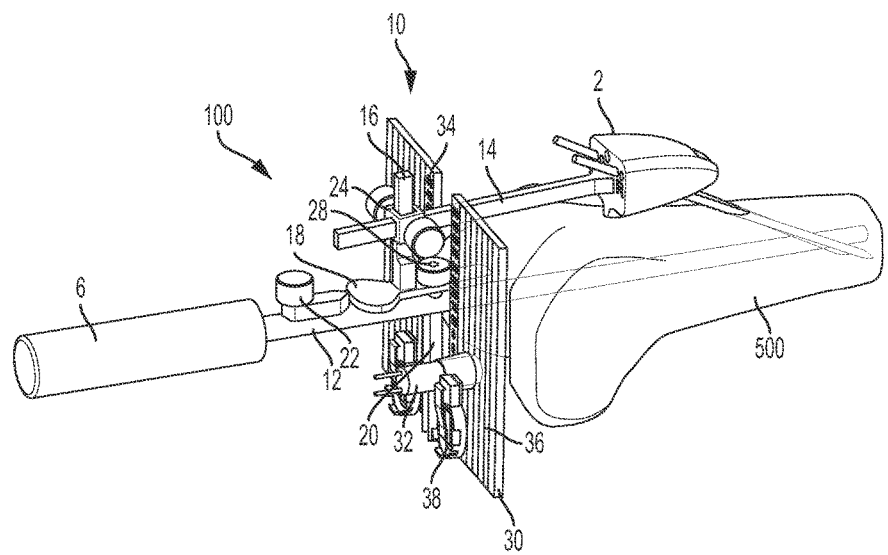
FIG. 1A is an isometric view of a datum block placement assembly and datum block affixed to a human femur in accordance with embodiments of the present disclosure.

Reference will now be made to the embodiments illustrated in the drawings and described in the following specification. It is understood that no limitation to the scope of this disclosure is thereby intended. The detailed description is to be construed as illustrative only and does not describe every possible embodiment since describing every possible embodiment would be impractical, if not impossible, and it will be understood that any feature, characteristic, component, composition, step or methodology described herein can be deleted, combined with or substituted for, in whole or part, any other feature, characteristic, component, composition, step or methodology described herein. Numerous alternative embodiments could be implemented, using either current technology or technology developed after the filing date of this patent, which would still fall within the scope of the claims. It is further understood that the scope of the present disclosure includes any alterations and modifications to the illustrated embodiments and includes further applications of the principles of this disclosure as would normally occur to one skilled in the art to which this disclosure pertains.

DETAILED DESCRIPTION

With reference to FIGS. 1A, 1B, 1C, 5A, and 5B, a positioning and template system for preparing a human femur 500 for knee replacement is shown. The positioning and template system include a datum block 2, a datum block placement assembly 100, and a cutting template assembly 200. The datum block 2 provides a positioned base for attachment of the cutting template assembly 200 to precisely locate the various femoral cuts in a knee replacement procedure. The datum block placement assembly 100 locates the datum block 2 into the correct position relative to a variety of anatomical features of the patient's femur 500. The positioning of the datum block 2 is at a known, fixed, and measured dimensional point in space referenced from key dimensions unique to each patient's individual femur.

The datum block placement assembly 100 is configured to locate and position the datum block 2 on a human femur 500. Specifically, the datum block placement assembly 100 positions the datum block 2 on the human femur 500 in a measured position relative to the transepicondylar axis (TEA) of the human femur 500. Further, the datum block placement assembly 100 is reversibly attachable to the datum block 2. As such, subsequent to placement of the datum block 2, the datum block placement assembly 100 may be detached from the datum block 2 leaving the datum block 2 correctly positioned on the human femur 500. The datum block 2 serves as a fixed base for subsequent attachment of the cutting template assembly 200. As such, the cutting template assembly 200 is reversibly attachable to the datum block 2 in place of the datum block placement assembly 100. Precisely positioning the datum block 2 allows the cutting template assembly 200 to be attached to the datum block 2 in the correct position to allow all necessary cuts to be made to the human femur 500 in preparation for a knee replacement procedure.

Figure 2A:
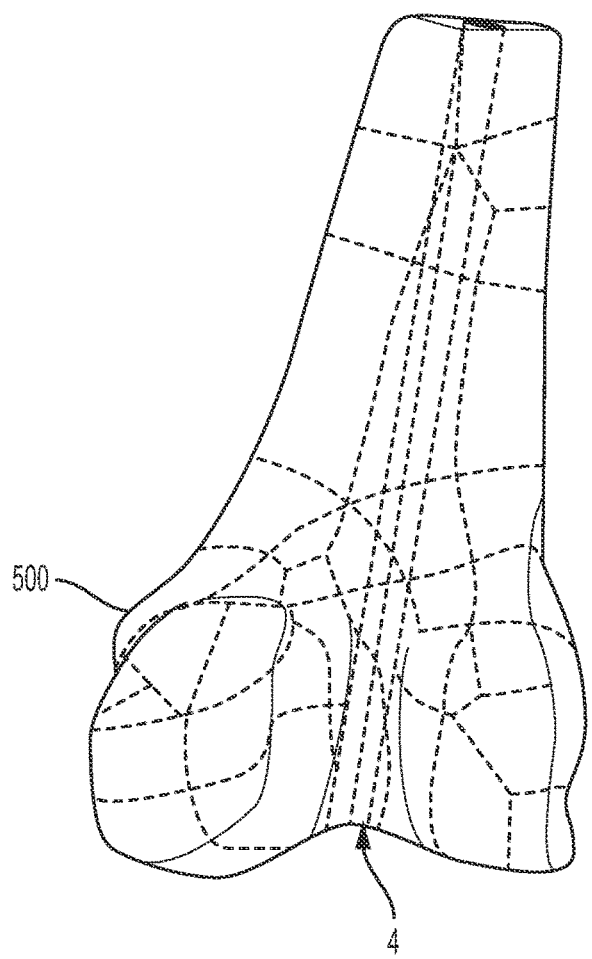
FIG. 2A is an end view of the distal end of an exemplary human femur with a centramedullary hole formed therein.
Figure 2B:
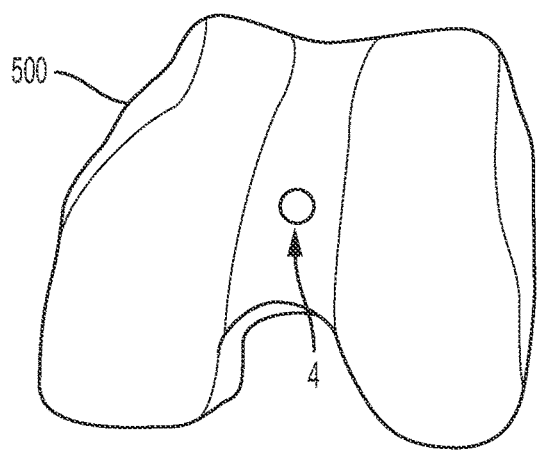
FIG. 2B is a top view of the distal end of an exemplary human femur with a centramedullary hole formed therein.

In various embodiments, the datum block placement assembly 100 attaches to a human femur via a centramedullary hole 4 formed along the length of the femur. With reference to FIGS. 2A and 2B, a centramedullary hole 4 is shown on an exemplary human femur. As used herein, the term 'centramedullary' is hereby defined to mean centrally located with respect to the medullary cavity of a long bone. The centramedullary hole 4 may be drilled or formed using other techniques known to orthopedic surgeons. The centramedullary hole 4 should maintain a parallel alignment to the femur sidewalls along the major axis of the femur.

Figure 1B:
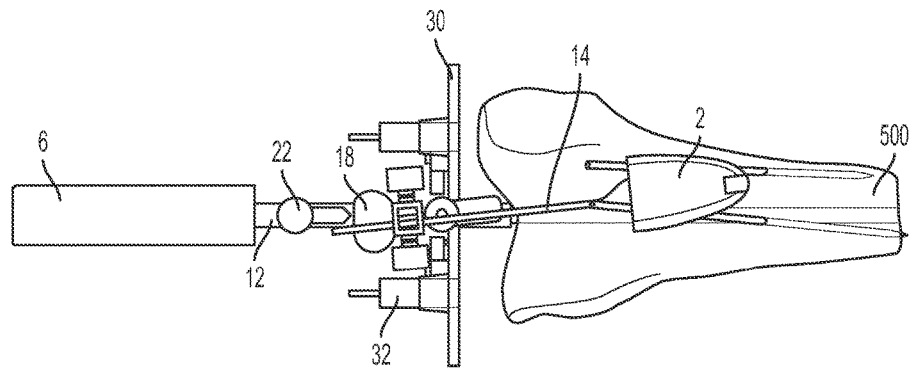
FIG. 1B is a top view of a datum block placement assembly and datum block affixed to a human femur in accordance with embodiments of the present disclosure.
Figure 1C:
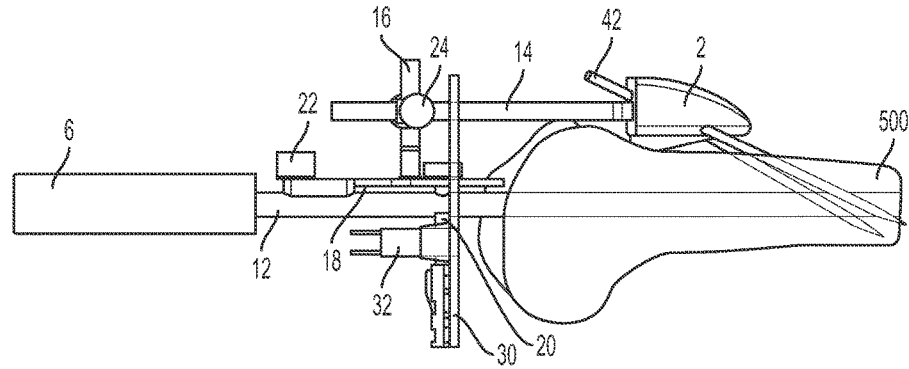
FIG. 1C is a side view of a datum block placement assembly and datum block affixed to a human femur in accordance with embodiments of the present disclosure.

Referring to the embodiment of FIGS. 1A, 1B, and 1C, the datum block placement assembly 100 includes an alignment rod 6, a datum block spatial positioning assembly 10, and a measurement base 30.

In at least one embodiment, the alignment rod 6 is configured to be inserted into the centramedullary hole 4 in the human femur 500. As the alignment rod 6 is utilized as a stable base during positioning of the datum block 2, stability of the alignment rod 6 is desirable. In various embodiments, the diameter of the alignment rod 6 is up to 2 millimeters (mm) larger than the diameter of the centramedullary hole 4, or 1 mm smaller to 1 mm larger than the diameter of centramedullary hole 4, or up to 2 mm smaller than the diameter of the centramedullary hole 4.

The datum block spatial positioning assembly 10 is configured to adjust the vertical (anterior-posterior), horizontal (proximal-distal), and rotational placement of the datum block 2 relative to the alignment rod 6. In at least one embodiment, the datum block spatial positioning assembly 10 includes an alignment rod mount 12, a horizontal locator beam 14, a vertical locator beam 16, a valgus adjustment plate 18, and a measurement base vertical beam 20. These multiple elements provide the adjustments needed to adjust the placement of the datum block 2 relative to the alignment rod 6.

In at least one embodiment the alignment rod mount 12 includes a cylindrical tube sized to fit around the alignment rod 6. The alignment rod mount 12 may rotate about the alignment rod 6 as well as translate along the length of the alignment rod 6. Additionally, the alignment rod mount 12 may include an alignment rod mount lock 22. The alignment rod mount lock 22 is configured to secure the alignment rod mount 12 to the alignment rod 6 and prevent rotation about the alignment rod 6 and/or translation along the length of the alignment rod 6. In various embodiments, the alignment rod mount lock 22 may be a finger screw which provides frictional interference against the alignment rod 6 when tightened, a cam-lock, a set screw, or other locking means familiar to the medical device industry.

The horizontal locator beam 14 and the vertical locator beam 16 provide horizontal (proximal-distal) and vertical (anterior-posterior) adjustment of the datum block 2 relative to the alignment rod 6. In at least one embodiment, the horizontal locator beam 14 and the vertical locator beam 16 are connected by a locator cross bar lock 24. The locator cross bar lock 24 provides a locking mechanism to secure the horizontal locator beam 14 and the vertical locator beam 16 in relationship to each other, yet allows relative translation of the horizontal locator beam 14 and the vertical locator beam 16 when in an unlocked position. In various embodiments, the locator cross bar lock 24 may be a housing with at least one finger screw which provides frictional interference against the horizontal locator beam 14 and/or the vertical locator beam 16 when tightened, at least one cam-lock, at least one set screw, or other locking means familiar to the medical device industry. In at least one embodiment, the locator cross bar lock 24 comprises at least one finger screw, or other locking means, to secure the horizontal locator beam 14 and at least one finger screw, or other locking means, to secure the vertical locator beam 16.

In accordance with embodiments of this disclosure, a surgeon may attach the datum block placement assembly 100 to the human femur 500 by inserting into the centramedullary hole 4 the alignment rod 6 with the datum block spatial positioning assembly 10 mated to the alignment rod 6. With reference to FIGS. 1A, 1B, and 1C, the datum block placement assembly 100 is shown in position relative to the human femur 500. The horizontal locator beam 14 of the datum block spatial positioning assembly 10 generally is initially retracted away from the human femur 500 but is shown extended in FIGS. 1A-1C. In at least one embodiment, the datum block 2 is reversibly mated with the horizontal locator beam 14 prior to any adjustments being made to the alignment rod 6, vertical locator beam 16, horizontal locator beam 14, or rotation orientation of the alignment rod mount 12.

As an initial matter, a surgeon may set the angle of the measurement base 30 in relationship to the face of the human femur 500 to a desired valgus femur alignment with the valgus adjustment plate 18. This angulation of the measurement base 30 determines the angle of the final cut across the face of the human femur 500, otherwise known as the distal femur cut. In at least one embodiment, the valgus adjustment plate 18 rotatably affixes the alignment rod mount 12 to the vertical locator beam 16. Specifically, the valgus adjustment plate 18 is pivotally affixed to the alignment rod mount 12 such that the vertical locator beam 16, the horizontal locator beam 14, and the datum block 2 may pivot in relation to the alignment rod 6.

With reference to FIG. 1B, the valgus adjustment plate 18 is shown rotated such that the horizontal locator beam 14 is not parallel to the alignment rod 6. In the illustrated embodiment the angulation of the valgus adjustment plate 18, and as such the angulation of the distal femur cut of the human femur 500, is adjustable to 5, 6 or 7 degrees in relationship to the centerline of the alignment rod 6. In various embodiments, the valgus adjustment plate 18 may be configured to be adjustable between 1 and 20 degrees, as well as all other ranges within those bounds, in 2 degree increments, or 1 degree increments, or 0.5 degree increments, or 0.25 degree increments. Non-exhaustive examples include between 2 and 10 degrees, or 3 and 8 degrees, or 2 and 8 degrees, or 1 and 15 degrees in 1 degree increments. In further embodiments, the angulation of the valgus adjustment plate 18 is continuous with no predefined set-points. A variety of adjustment angles are contemplated to meet surgeon preferences and/or anatomical anomalies of various human femurs 500. When the angle for the distal femur cut is set, the valgus adjustment plate 18 is locked into position utilizing a valgus adjustment lock screw 28. In at least one embodiment, the valgus adjustment lock screw 28 is a finger screw which forces the valgus adjustment plate 18 against the alignment rod mount 12 to provide frictional interference between the valgus adjustment plate 18 and the alignment rod mount 12 when tightened, a cam-lock, a set screw, or other locking means familiar to the medical device industry. Upon securing the angle of the valgus adjustment plate 18, adjustment of the datum block spatial positioning assembly 10 is complete for the distal femur cut of the human femur 500 upon placement of the cutting template assembly 200.

Figure 4:
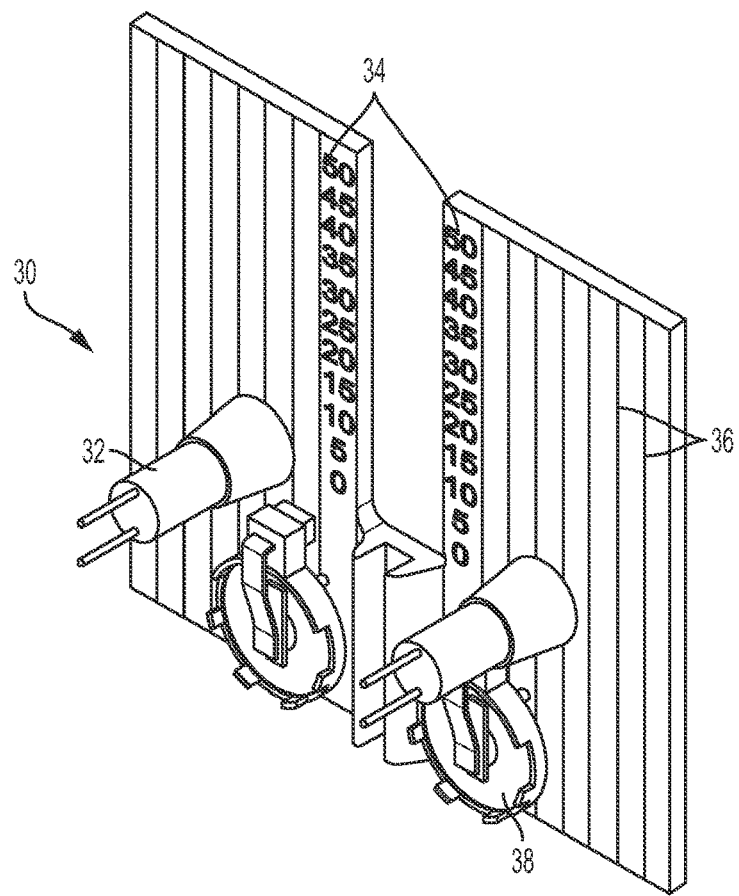
FIG. 4 is an isometric view of a measurement base of the datum block placement assembly in accordance with embodiments of the present disclosure.

In further embodiments, the measurement base 30 is slidably affixed to the datum block spatial positioning assembly 10. In specific embodiments, the measurement base 30 is slidably affixed to the measurement base vertical beam 20. In at least one embodiment, the measurement base vertical beam 20 is affixed to the alignment rod mount 12 in a direction opposite the vertical locator beam 16 as shown in FIG. 1A. The slidable connection between the measurement base 30 and the measurement base vertical beam 20 allows vertical translation (anterior-posterior) of the measurement base 30. With reference to FIG. 4, in various embodiments, the measurement base 30 comprises at least one alignment laser 32, for example, 1, 2, or 3 alignment lasers 32. The at least one alignment laser 32 is positioned on the measurement base 30 to project a straight line onto the human femur 500. Additionally, in at least one embodiment, the measurement base 30 comprises at least one battery holder to house a battery to power the at least one alignment laser 32. In further, embodiments, the alignment lasers 32 have internal batteries. In at least one embodiment, the alignment lasers 32 may be reversibly removed from the measurement base 30 for replacement or sterilization, for example.

In accordance with embodiments of this disclosure, a surgeon may activate the at least one alignment laser 32 located on the measurement base 30. The at least one alignment laser 32 projects a straight line upon the face of the human femur 500 which bisects the face of the human femur 500. A surgeon may then adjust the measurement base 30 until the projected laser lines are in alignment with the transepicondylar axis (TEA) of the human femur 500 by rotating the alignment rod mount 12 and affixed components of the datum block spatial positioning assembly 10 about the alignment rod 6 and translating the measurement base 30 along the measurement base vertical beam 20. In at least one embodiment, feet may be placed on the posterior aspect of the measurement base 30 to allow posterior referencing during sizing and rotational alignment. Once the proper orientation of the datum block spatial positioning assembly 10 in relationship to the transepicondylar axis is achieved, the rotation and translation of the datum block spatial positioning assembly 10 is locked by tightening the alignment rod mount lock 22. Upon securing the relative position of the alignment rod mount 12 and the alignment rod 6, the adjustment of the datum block spatial positioning assembly 10 is complete for the anterior femur cut of the human femur 500 upon placement of the cutting template assembly 200.

In an initial configuration the datum block 2 is positioned proximal to the measurement base 30 with the horizontal locator beam 14 substantially fully retracted. This configuration positions the datum block 2 between the measurement base 30 and the human femur 500. To further position the datum block 2, the horizontal locator beam 14 may be slid up the vertical locator beam 16 to adjust anterior-posterior positioning until the lower extreme of the datum block 2 rests on the anterior cortex of the human femur 500. Placement of the datum block 2 on the anterior cortex of the human femur 500 leaves the distal face of the human femur 500 clear for unobstructed cutting of the distal femur cut. Subsequently, a surgeon may advance the datum block 2 to the desired proximal-distal position on the human femur 500 by extending the horizontal locator beam 14 while maintaining the position of the locator cross bar lock 24 along the vertical locator beam 16. In at least one embodiment, the locator cross bar lock 24 comprises separate locks for the horizontal locator beam 14 and the vertical locator beam 16 such that the vertical locator beam 16 may be secured while allowing the horizontal locator beam 14 to extend and retract. The datum block 2 may then be inserted along the length of the human femur 500. In embodiments, a minimally invasive surgical technique may be utilized. The datum block 2 is now positioned and the vertical locator beam 16 position may be locked by tightening the locator cross bar lock 24.

Figure 3:
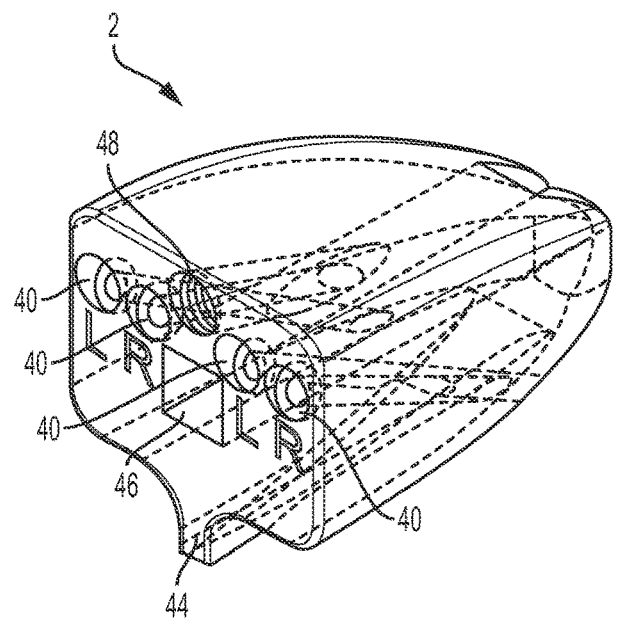
FIG. 3 is an isometric view of a datum block in accordance with embodiments of the present disclosure.

With reference to FIG. 3, an embodiment of the datum block 2 is detailed. In various embodiments the datum block 2 is fabricated from a single piece of machined surgical grade stainless steel, cobalt chrome molybdenum, titanium, or any other biocompatible material known to one having ordinary skill in the art. In various embodiments, the posterior of the datum block 2 is rounded and beveled to allow the datum block 2 to slip between the muscle tissue and human femur 500 for a minimally invasive soft tissue insertion.

In various embodiments, the datum block 2 has four through holes that run from the face of the datum block 2 proximal the datum block placement assembly 100 to the posterior side of the datum block 2. The through holes form bone pin securement shafts 40 which are configured to pass a bone pin 42 therethrough. Two of the bone pin securement shafts 40 are for use with the left femur cuts (may be designated with an "L" or other indicia) and two of the bone pin securement shafts 40 are for use with a right femur cut (may be designated with an "R" or other indicia). The angulation of the bone pin securement shaft 40 is skewed between left and right femur cuts to match the variation in anatomy between a right femur and a left femur. Each set of bone pin securement shafts 40 are designed to put the least amount of stress on the respective human femur 500 as a bone pin 42 is inserted to secure the datum block 2 to the human femur 500.

In at least one embodiment, the bone pins 42 are threaded pins and the interior of the bone pin securement shafts 40 of the datum block 2 are threaded with mating threads. Additionally, in various embodiments the bone pin securement shafts 40 are threaded only a portion of the length of the bone pin securement shafts 40. Non-limiting and non-exhaustive examples include approximately $\frac{1}{16}^{th}$ the length of the bone pin securement shafts 40, approximately $\frac{1}{8}^{th}$ the length of the bone pin securement shafts 40, approximately $\frac{1}{4}^{th}$ the length of the bone pin securement shafts 40, approximately $\frac{1}{2}$ the length of the bone pin securement shafts 40, and approximately $\frac{3}{4}^{th}$ the length of the bone pin securement shafts 40. The threaded bone pin 42 engages the threads of the datum block 2 and when secured to the human femur 500 serves as a method to lock the datum block 2 into position on the human femur 500.

In further embodiments the bone pin securement shafts 40 are unthreaded. As such, the bone pin securement shafts 40 are non-parallel. The skew orientation of each bone pin securement shaft 40 relative to the paired bone pin securement shaft 40 helps prevent the datum block 2 from translating along the bone pins 42 when secured to the human femur 500. In various embodiments, the angle between matched pairs of bone pin securement shafts 40 is up to 15°. Non-limiting and non-exhaustive examples include 1°, or 2°, or 3°, or 4°. Additionally, embodiments with threaded bone pin securement shafts 40, the bone pin securement shafts 40 may also be non-parallel.

On the posterior side of the datum block 2 (side facing the human femur 500), in multiple embodiments, a center foot 44 is formed along the centerline of the datum block 2. The center foot 44 on the datum block 2 may serve as an extension probe for measuring the alignment and proximity of the anterior femoral chamfer cut as well as determining accurate sizing and alignment of the datum block placement assembly 100 and subsequently the cutting template assembly 200 and implant. The center foot 44 also serves as a stabilization point for the datum block 2 prior to securing the datum block 2 to the human femur 500 with the bone pins 42.

Additionally, in at least one embodiment, the datum block 2 has a datum engagement hole 46 on the face of the datum block 2 proximal the datum block placement assembly 100 that serves as the docking interface of the horizontal locator beam 14 of the datum block placement assembly 100 and a cutting jig main beam 210 of the cutting template assembly 200. The datum engagement hole 46 is sized and shaped to mate with the size and shape of the ends of the horizontal locator beam 14 and the cutting jig main beam 210. Either the horizontal locator beam 14 or the cutting jig main beam 210 can be inserted into the datum block 2 and the datum block 2 is held secure to the horizontal locator beam 14 or the cutting jig main beam 210 by tightening a securing screw 48 located adjacent the datum engagement hole 46. The securing screw 48 can be loosened which allows for the release of the horizontal locator beam 14 or the cutting jig main beam 210 from the datum block 2.

In accordance with at least one embodiment, bone pins 42 are pre-loaded into the bone pin securement shafts 40 before positioning the datum block 2 on the human femur 500. Subsequently, upon positioning the datum block 2 on the human femur 500, a surgeon may utilized the bone pins 42 that are pre-loaded into the datum block 2 to affix the datum block 2 into position. When the bone pins 42 are fully placed into the human femur 500, the datum block 2 is locked into position on the human femur 500. The datum block 2 is set for the major femoral cuts including the distal femur cut, the anterior femur cut, the posterior femur cut, the anterior chamfer cut, and the posterior chamfer cut upon installation of the cutting template assembly 200.

In accordance with embodiments of the present disclosure, a surgeon may utilize the measurement base 30 to determine the appropriately sized cutting template assembly 200. With reference to FIG. 4, the measurement base 30 is marked with measurement indicia 34. The measurement indicia 34 are placed on the measurement base 30 through, for example, etching, printing, or other marking means known to one having skill in the art. In at least one embodiment, the measurement indicia 34 are a series of numerals at 5 mm spacing. The measurement indicia 34 provide the surgeon a scale for referencing the spacing of aspects of the positioning and template system as well as the spacing of aspects of the human femur 500. In at least one embodiment, the measurement base 30 additionally includes width indicia 36 which provide a relative scale for measurement of the horizontal distance across the human femur 500. The width indicia 36 may be a series of etched or printed vertical lines at a known spacing across the face of the measurement base 30. By looking through the measurement base 30, a surgeon may determine the approximate width of the human femur 500 and verify the medial-lateral size of the implant.

In various embodiments the measurement base 30 is fabricated from a clear or transparent polymer, such as a polycarbonate, which provides visualization of the human femur 500 behind the measurement base 30. In further embodiments, the measurement base 30 may be fabricated from an opaque material, such as 316L stainless steel, a Co—Cr alloy, titanium, $Ti_6Al_4V$, nylon 12, or polyether ether ketone (PEEK).

In at least one embodiment, to determine the appropriate size cutting template assembly 200, the measurement base 30 is adjusted along the measurement base vertical beam 20 until the projected laser line from the alignment lasers 32 bisects the center axis of the alignment rod 6. Using the measurement indicia 34 etched upon the measurement base 30 and referencing a landmark on the datum block placement assembly 100, a surgeon may determine sizing information for the appropriately sized cutting template assembly 200. In at least one embodiment the landmark on the datum block placement assembly 100 is the side of the horizontal locator beam 14 proximal the human femur 500 (the bottom of the horizontal locator beam 14). It will be appreciated that other landmarks on the datum block placement assembly 100 may be utilized by adjusting the scale of the measurement indicia 34 accordingly. In various embodiments the measurement indicia 34 directly identifies the appropriately sized cutting template assembly 200. In further embodiments, the measurement indicia 34 provide a reference indicator which is correlated with a look-up table or other reference guide to indicate the appropriately sized cutting template assembly 200. In further embodiments, the measurement indicia on the measurement base 30 correspond to the sizing of a specific or multiple manufacturers' knee implants.

After the surgeon has the sizing information for the cutting template assembly 200 and the datum block 2 is secured by the bone pins 42, the surgeon removes the datum block placement assembly 100 from the datum block 2, by disconnecting the horizontal locator beam 14 from the datum block 2 and removing the entire datum block placement assembly 100 from the human femur 500 including the alignment rod 6. After the datum block placement assembly 100 is removed, all that remains on the human femur 500 is the datum block 2 in the desired placement and orientation for the femoral cuts.

Figure 5A:
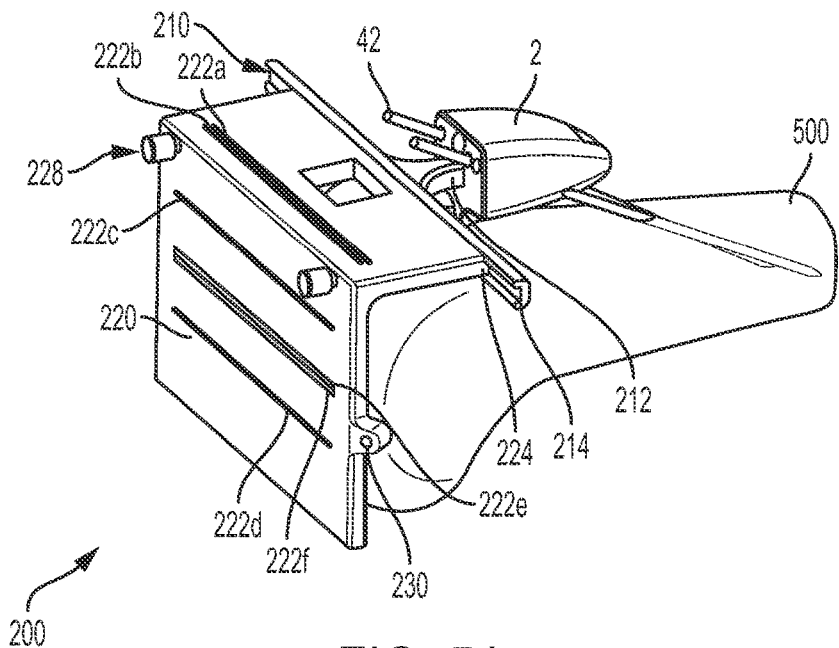
FIG. 5A is a front isometric view of a cutting template assembly and datum block affixed to a human femur in accordance with embodiments of the present disclosure.
Figure 5B:
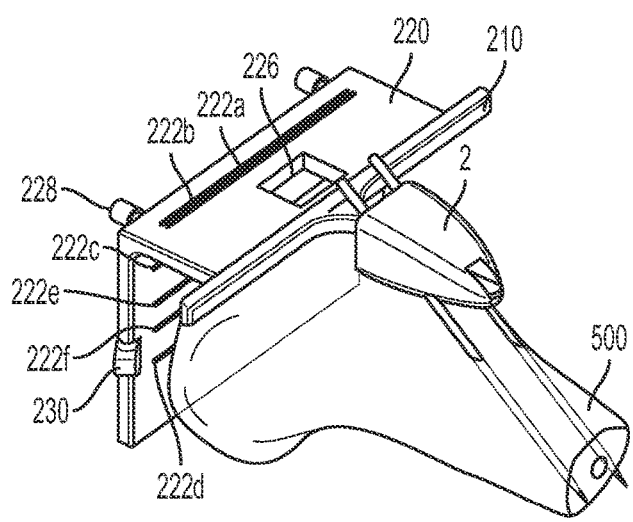
FIG. 5B is a rear isometric view of a cutting template assembly and datum block affixed to a human femur in accordance with embodiments of the present disclosure.

With reference to FIGS. 5A and 5B, the cutting template assembly 200 includes a cutting jig main beam 210 and a cutting template 220. The cutting template 220 provides a guide for the placement and angulations of the major femoral cuts in knee replacement surgery, including the distal femur cut, the anterior femur cut, the posterior femur cut, the anterior chamfer cut, and the posterior chamfer cut, each of which is familiar to one skilled in the art. The cutting template 220 includes a plurality of cutting template guide slots 222. With reference to FIGS. 5A and 5B, the cutting template guide slots 222 include at least one distal femur cut guide slot 222*a*/222*b*, at least one anterior femur cut guide slot 222*c*, at least one posterior femur cut guide slot 222*d*, at least one anterior chamfer cut guide slot 222*e*, and at least one posterior chamfer cut guide slot 222*f*. The cutting template guide slots 222 are sized to allow the blade of a surgical saw to pass therethrough.

Using the sizing data obtained from the measurement indicia 34 on the measurement base 30, the appropriate cutting template assembly 200 sized for the patient's femur 500 may be selected. The cutting jig main beam 210 is configured to be reversibly attached to the datum block 2. For example, a cutting jig tab 212 on the cutting jig main beam 210 is sized to fit into the datum engagement hole 46 of the datum block 2 and reversibly attach the cutting jig main beam 210 to the datum block 2. The cutting jig tab 212 is inserted into the datum engagement hole 46 until the cutting template 220 is touching the human femur 500. Subsequently, the securing screw 48 on the datum block 2 may be tightened to secure the cutting template assembly 200 into the datum block 2. Since the datum block 2 is fixed into the correct orientation, the cutting template assembly 200 and likewise the cutting template 220 are already in the correct orientation for all of the major femoral cuts.

In at least one embodiment, the cutting template 220 is slidably attached to the cutting jig main beam 210 to allow medial-lateral positioning of the cutting template. The cutting jig main beam 210 includes a keyed channel 214 and the cutting template 220 includes a mating keyed edge 224. The keyed edge 224 of the cutting template 220 may be slid into the keyed channel 214 of the cutting jig main beam 210. In further embodiments, the cutting template 220 and the cutting jig main beam 210 are mated during manufacture of the cutting template assembly 200 and stops are provided at the extremes of the keyed channel 214 to prevent removal of the cutting template 220.

The cutting template 220 is free to slide along the cutting jig main beam 210. A surgeon may slide the cutting template 220 along the cutting jig main beam 210 until a notch cut guide aperture 226 (representing the notch cut for posterior stabilized implants) on the anterior side of the cutting template 220 is at the preferred ML (medial-lateral) alignment. The notch cut is traditionally only necessary for posterior stabilized knee implants. The precise desirable positioning of the notch cut guide aperture 226 and the resulting notch cut would be understood by one of skill in the art and may be adjusted based on factors external to the present disclosure such as specific manufacturer's knee implant systems and/or surgeon's personal technique or preference.

When a surgeon has the cutting template 220 positioned in the desired medial-lateral location along the cutting jig main beam 210, the surgeon may then tightens a pair of cutting jig lock screws 228 on the distal face of the cutting template 220. Tightening the cutting jig lock screws 228 secures the cutting template 220 in position and prevents the cutting template 220 from sliding on the cutting jig main beam 210. In various embodiments, the cutting jig lock screws 228 may be a pair of finger screws which provides frictional interference against the cutting jig main beam 210 when tightened, at least one cam-lock, at least one set screw, or other locking means familiar to the medical device industry.

In various embodiments, the cutting template further comprises at least one bone pin anchor 230 through which a bone pin 42 may added to secure and stabilize the cutting template 220 relative to the human femur 500. The bone pin 42 may be threaded or unthreaded in various embodiments and as such the bone pin anchor 230 may be threaded or unthreaded in various embodiments. The positioning and alignment of the at least one bone pin anchor 230 should locate inserted bone pins 42 outside of the cutting arc of the surgeon's bone saw.

With the cutting template assembly 200 in place and secured, a surgeon may make all of the appropriate cuts on the human femur 500 using the cutting template 220. These cuts include the distal femur cut, the anterior femur cut, the posterior femur cut, anterior chamfer cuts, and posterior chamfer cuts, in addition to the notch cut for posterior stabilizing knee designs. Utilizing the cutting template assembly 200 allows all the cuts in preparation for a knee replacement to be made in one setting with no required repositioning of bone pins 42 or utilization of a plurality of sequential jigs or templates. A single cutting template 220 provides the cutting template guide slots 222 for all the required cuts.

In various embodiments the cutting template 220 is fabricated from a clear or substantially transparent biocompatible material to allow the surgeon to view the human femur 500 as the cuts are performed. An exemplary, non-limiting, clear or substantially transparent biocompatible material is polycarbonate.

In further embodiments the cutting template 220 is fabricated from 316L stainless steel, a Co—Cr alloy, titanium, $Ti_6Al_4V$, or nylon 12. One having skill in the art will appreciate that this list is non-exhaustive and other materials commonly used for surgical implants and/or instrumentation are equally applicable for fabrication of the cutting template 220

After all required cuts are made a surgeon may remove all the bone pins 42. In the various embodiments the bone pins 42 to be removed may include the bone pin(s) 42 placed in the cutting template 220 and the bone pins 42 holding the datum block 2 in place. Upon removal of all the bone pins 42, the cutting template assembly 200 and the datum block 2 are free from the human femur 500. A surgeon may simply grasp the cutting template assembly 200 while still attached to the datum block 2 and pull it free of the human femur 500, thus removing the datum block 2 from the human femur 500 as well as the cutting jig main beam 210 and the cutting template 220.

Exemplary Surgical Technique:

After gaining exposure of the distal femur 500 by making an incision over the anterior knee and then medial to the patella, which is moved laterally, a drill is used to open the intramedullary canal of the human femur 500 just anterior to the PCL insertion. Using a surgical marking pen and a straight edge, the transepicondylar axis (TEA) is marked. This line is then visually compared to the posterior condyles to confirm an appropriate amount of external rotation. A hand reamer is then used to ream the intramedullary canal of the human femur 500 to accept the alignment rod 6. The alignment rod 6 with the datum block placement assembly 100 attached is then placed within the canal with the valgus angle set per the surgeon's preference using the valgus adjustment plate 18 and valgus adjustment lock screw 28. The vertical locator beam 16 and horizontal locator beam 14 are initially positioned so that the datum block 2 can clear the anterior femur 500 as the alignment rod 6 is placed into the intramedullary canal of the human femur 500.

Using a horizontal laser line projected from the at least one alignment laser 32 as a reference, the datum block spatial positioning assembly 10 is rotated around the alignment rod 6 until the laser line is parallel to the transepicondylar axis (TEA). The datum block spatial positioning assembly 10 is then locked in place by tightening the alignment rod mount lock 22.

With the rotation of the datum block spatial positioning assembly 10 now set relative to the alignment rod 6, the vertical locator beam 16 and the horizontal locator beam 14 are adjusted to bring the datum block 2 down until the center foot 44 (feeler point) on the posterior aspect of the datum block 2 contacts the anterior side of the human femur 500. In addition to providing stability to the datum block 2, the center foot 44 also sets the datum block reference point for the anterior femoral cut. The positioning of the horizontal locator beam 14 and the vertical locator beam 16 is then locked in place using the locator cross bar lock 24.

Now that the datum block 2 has been placed in the correct valgus alignment from the alignment rod 6, correct rotational alignment from the alignment lasers 32 reference to the TEA, and correct alignment relative to the anterior side of the human femur 500 from positioning of the center foot 44 of the datum block 2, the datum block 2 is locked in place with two bone pins 42 placed through the datum block 2 and into the femoral shaft proximal to the area of the anterior femoral cut to be made later. The cutting template assembly 200 size is then determined by lowering the measurement base 30 until the at least one alignment laser 32 references the surgeon's desired amount of bone to be removed from the posterior femoral condyles as dictated by the particular implant. The surgeon uses the measurement indicia 34 etched upon the measurement base 30 referenced to the bottom of the horizontal locator beam 14 to determine the appropriate size cutting template assembly 200 and implant component size. Width indicia 36 as vertical lines are also referenced on the measurement base 30 to show the medial/lateral dimension of the component size as a secondary check. Now that the size has been determined the securing screw 48 connecting the datum block 2 to the horizontal locator beam 14 is loosened and the datum block placement assembly 100 is removed along with the alignment rod 6 leaving the datum block 2 in place.

The cutting template assembly 200 with the appropriate sized cutting template 220 is then placed into the datum block 2 and brought into contact with the distal end of the human femur 500. The securing screw 48 in the datum block 2 is then tightened to secure the cutting template assembly 200 to the datum block 2. If the surgeon plans to make a box cut for a PCL substituting type of implant, the cutting template 220 is centered on the human femur 500 in the medial lateral plane by adjusting along the cutting jig main beam 210. The cutting jig lock screws 228 are tightened to secure the cutting template 220 in the desired position on the cutting jig main beam 210. The surgeon then tests the stability of the cutting template assembly 200 and cutting template 220 which will vary depending on the patient's bone quality. If the cutting template assembly 200 is at all unstable one or two bone pins 42 may be placed into the human femur 500 through the bone pin anchors 230 on the cutting template 220. Using an oscillating saw all bone cuts are then made through the cutting template guide slots 222 of the cutting template 220. The cutting template assembly 200 is removed from the datum block 2 followed by removal of the bone pins 42 in the datum block 2 along with the datum block 2 itself. The femoral trial component is then placed as per the standard technique.

While exemplary embodiments of the procedure is provided above, one of ordinary skill in the art would understand that individual surgical technique and surgeon preferences may result in variations to the procedure while maintaining the spirit and novel aspects thereof. As such other known and accepted methods or techniques for performing steps outlined within the technique may be substituted where appropriate.

While reference is made throughout this disclosure to specific means of achieving a desired result, it is to be understood that alternatives known to one skilled in the art are equally contemplated.

While particular embodiments of the present disclosure have been illustrated and described, it would be obvious to those skilled in the art that various other changes and modifications can be made.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential unless so stated.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the disclosure or to imply that certain features are critical, essential, or even important to the structure or function of embodiments of the disclosure. Rather, these terms are merely intended to identify particular aspects of an embodiment of the present disclosure or to emphasize alternative or additional features that may or may not be utilized in a particular embodiment of the present disclosure.

For the purposes of describing and defining embodiments of the present disclosure it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

What is claimed is:

1. A positioning and template system for preparing a femur for knee replacement, the system comprising:
    a datum block;
    a datum block placement assembly comprising
        an alignment rod configured to be inserted into a drilled hole centramedullary in the femur;
        a datum block spatial positioning assembly to adjust the vertical, horizontal, and rotational placement of the datum block relative to the alignment rod; and
        a measurement base slidably affixed to the datum block spatial positioning assembly and configured to measure the size of a cutting template for positioning the location and defining the angle of cuts to the femur; and
    a cutting template assembly;
    wherein,
        the datum block placement assembly is reversibly attachable to the datum block,
        the datum block placement assembly positions the datum block on the femur in a measured position relative to the transepicondylar axis of the femur when the datum block placement assembly is attached to the datum, and
        the cutting template assembly is reversibly attachable to the datum block in place of the datum block placement assembly.

2. The system of claim 1, wherein the datum block comprises at least two bone pin securement shafts configured to pass a bone pin therethrough for fixation to the femur.

3. The system of claim 2, wherein the bone pin securement shafts are non-parallel.

4. The system of claim 2, wherein the bone pin securement shafts are threaded.

5. The system of claim 1, wherein the datum block spatial positioning assembly comprises:
    an alignment rod mount comprising a cylindrical tube disposed around the alignment rod such that the alignment rod mount may rotate about the alignment rod;
    a horizontal locator beam configured to be reversibly attached to the datum block;
    a vertical locator beam slidably attached to the horizontal locator beam;
    a valgus adjustment plate rotatably affixing the vertical locator beam to the alignment rod mount such that the horizontal locator beam, the vertical locator beam, and the valgus adjustment plate may rotate relative to the alignment rod mount; and
    a measurement base vertical beam affixed to the alignment rod mount in a direction opposite the vertical locator beam.

6. The system of claim 5, wherein the measurement base is slidably affixed to the measurement base vertical beam.

7. The system of claim 1, wherein the measurement base comprises at least one alignment laser positioned to project a straight line onto the femur.

8. The system of claim 1, wherein the measurement base comprises indicia to indicate the appropriate size of the cutting template.

9. The system of claim 1, wherein the cutting template assembly comprises:
    a cutting jig main beam configured to be reversibly attached to the datum block; and
    a cutting template slidably attached to the cutting jig main beam to allow medial-lateral positioning of the cutting template,
    wherein the cutting template comprises a plurality of cutting template guide slots for defining the position and angle of a distal femur cut, an anterior femur cut, a posterior femur cut, an anterior chamfer cut, and a posterior chamfer cut.

10. The system of claim 9, wherein the cutting template further comprises a notch cut guide aperture for defining the position and cutting boundaries of a notch cut for posterior stabilizing knee implants.

11. The system of claim 9, wherein the cutting template further comprises at least one bone pin anchor for securement of the cutting template to the femur with bone pins.

12. The system of claim 11, wherein the bone pin anchor is positioned along the medial or lateral edge of the cutting template.

13. The system of claim 9, wherein the plurality of cutting template guide slots are positioned such that repositioning of the cutting template between cuts is not required.

14. A method of preparing a femur for knee replacement comprising:
 positioning a datum block on the femur in a measured position relative to the transepicondylar axis of the femur with a datum block placement assembly, the datum block placement assembly comprising:
  an alignment rod configured to be inserted into a drilled hole centramedullary in the femur;
  a datum block spatial positioning assembly to adjust the vertical, horizontal, and rotational placement of the datum block relative to the alignment rod; and
  a measurement base slidably affixed to the datum block spatial positioning assembly and configured to measure the size of a cutting template for positioning the location and defining the angle of cuts to the femur, wherein the datum block placement assembly is reversibly attachable to the datum block;
 securing the datum block to the femur;
 removing the datum block placement assembly from the secured datum block;
 attaching a cutting template assembly comprising a cutting template to the secured datum block, wherein the cutting template assembly is reversibly attachable to the datum block in place of the datum block placement assembly; and
 cutting a distal femur cut, an anterior femur cut, a posterior femur cut, an anterior chamfer cut, and a posterior chamfer cut on the femur using a plurality of cutting template guide slots provided on the cutting template to define the position and angle of the distal femur cut, the anterior femur cut, the posterior femur cut, the anterior chamfer cut, and the posterior chamfer cut,
 wherein the plurality of cutting template guide slots are positioned such that repositioning of the cutting template between cuts is not required.

15. The method of claim 14,
 wherein the measurement base comprises at least one alignment laser positioned to project a straight line onto the femur.

16. The method of claim 15, wherein positioning the datum block on the femur comprises:
 forming a hole centramedullary in the femur;
 inserting the alignment rod into the formed hole; and
 adjusting the vertical, horizontal, and rotational placement of the datum block relative to the alignment rod by:
  (a) adjusting the valgus alignment of the measurement base such that the measurement base aligns with a plane parallel to a plane of the desired distal femur cut,
  (b) rotating the datum block placement assembly around the alignment rod and adjusting the vertical placement of the measurement base to align the projected straight line from the at least one alignment laser with the transepicondylar axis of the femur, and
  (c) adjusting the vertical and horizontal placement of the datum block by adjusting a horizontal locator beam and a vertical locator beam which connect the datum block to the alignment rod such that the datum block rests on the anterior cortex of the femur.

17. The method of claim 16, wherein the method further comprises determining the appropriate size of cutting template by:
 adjusting the position of the measurement base such that the alignment lasers bisect the center axis of the alignment rod, and
 reading a measurement from indicia on the measurement base corresponding with a landmark on the datum block placement assembly.

18. The method of claim 17, wherein the landmark on the datum block placement assembly is a side of the horizontal locator beam proximal the femur.

19. The method of claim 14, wherein securing the datum block to the femur comprises inserting bone pins into bone securement slots on the datum block, where the bone securement pins are non-parallel.

* * * * *